US006610884B2

United States Patent
Gerle et al.

(10) Patent No.: US 6,610,884 B2
(45) Date of Patent: Aug. 26, 2003

(54) POLYCARBOXYLIC ACIDS, PREPARATION THEREOF AND USE THEREOF FOR TREATING CELLULOSIC FIBRES OR TEXTILE OR PAPER MATERIALS PRODUCED THEREFROM

(75) Inventors: Michael Gerle, Bergheim (DE); Hans-Albert Ehlert, Singapore (SG); Günter Franke, Leichlingen (DE); Helmut-Martin Meier, Ratingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/764,185

(22) Filed: Jan. 17, 2001

(65) Prior Publication Data
US 2001/0018542 A1 Aug. 30, 2001

(30) Foreign Application Priority Data
Jan. 24, 2000 (DE) .......................... 100 02 877

(51) Int. Cl.⁷ ..................... C07C 51/31; C07C 61/08
(52) U.S. Cl. .................... 562/509; 562/523; 562/526; 562/524
(58) Field of Search .................. 562/523, 524, 562/526, 509

(56) References Cited

U.S. PATENT DOCUMENTS

| | | | |
|---|---|---|---|
| 3,646,130 A | 2/1972 | Parshall | 260/533 C |
| 4,532,079 A | 7/1985 | Venturello et al. | 260/413 |
| 4,550,196 A | 10/1985 | Venturello et al. | 562/418 |
| 4,833,272 A | 5/1989 | Nakazawa et al. | 562/523 |
| 5,047,582 A | 9/1991 | Brotherton et al. | 562/508 |
| 5,137,537 A * | 8/1992 | Herron et al. | 8/120 |
| 5,205,836 A | 4/1993 | Hansen et al. | 8/120 |
| 5,591,893 A | 1/1997 | Kulpe et al. | 562/504 |

FOREIGN PATENT DOCUMENTS

| | | | |
|---|---|---|---|
| CA | 1138891 | 1/1983 | |
| EP | 0432797 A2 * | 12/1990 | .......... C07C/61/24 |
| EP | 0 688 897 | 12/1995 | |
| EP | 0 690 937 | 10/1999 | |
| JP | 59-128350 | 7/1984 | |
| JP | 62-270785 | 11/1987 | |
| JP | 2-197586 | 8/1990 | |
| JP | 2-254182 | 10/1990 | |
| JP | 8-295649 | 11/1996 | |

OTHER PUBLICATIONS

Text. Res. Journal, Nov. 1967, Rowland et al, pp. 933–941, Introduction of Ester Cross Links into Cotton Cellulose by a Rapid Curing Process.
J. Org. Chem., vol. 30, (month unavailable) 1965, pp. 1488–1491, Franz et al, Mechanism of the Nitric Acid Oxidation of Olefins.
"A convenient, Mild method for Oxidative Cleavage of Alkenes with Jones Reagent/ Osmium Tetraoxide" Henry and Weinreb, J Org. Chem. vol. 58(17), p. 4745 (1993).*

* cited by examiner

Primary Examiner—Richard L. Raymond
Assistant Examiner—Zachary C. Tucker
(74) Attorney, Agent, or Firm—Godfried R. Akorli; Diderico van Eyl

(57) ABSTRACT

A process is provided for preparing specific polycarboxylic acids by oxidative cleavage of double-bond compounds with hydrogen peroxide or hydrogen peroxide donors. The polycarboxylic acids thus obtained are notable for excellent acid stability, and consequently ease of handling in aqueous solution and are useful for treating cellulosic fibers or textile or paper materials produced therefrom.

23 Claims, No Drawings

POLYCARBOXYLIC ACIDS, PREPARATION THEREOF AND USE THEREOF FOR TREATING CELLULOSIC FIBRES OR TEXTILE OR PAPER MATERIALS PRODUCED THEREFROM

The invention relates to acid-stable polycarboxylic acids, to a process for their preparation by oxidative cleavage of double-bond compounds with hydrogen peroxide or hydrogen peroxide donors, to the use of the polycarboxylic acids for treating cellulosic fibres or textile or paper materials produced therefrom and to the thusly treated cellulosic fibres, textile materials or paper materials.

Textiles made of cellulosic fibres such as cotton have the advantage over synthetic fibres of being hydrophilic, which manifests itself in high moisture absorption and good wear comfort. The reason for the high moisture absorption is the swellable amorphous regions in cellulosic fibres. However, cellulose swollen by washing or perspiration wrinkles and has to be smoothed again by thermal and mechanical treatment. In addition, cotton shrinks on washing, causing textiles to lose their original shape. To control these disadvantages, cellulosic fibres have for many years been treated with products which, by reacting with the hydroxyl groups of the cellulose, partly crosslink the amorphous parts of the fibres. Owing to this treatment, the textile retains its shape on wearing and washing. Preferred crosslinkers are methylolated urea or melamine derivatives. The disadvantage with these compounds is that they may release formaldehyde in the course of the finishing and use of the textile.

There has therefore been no shortage of attempts to find alternative and ecologically better products for treating textiles. The use of polycarboxylic acids such as butanetetracarboxylic acid for formaldehyde-free textile finishing is known in principle from Text. Res. J. 37, 933 (1967) and U.S. Pat. No. 4,820,307.

It is likewise already known in principle that polycarboxylic acids may be prepared by oxidative cleavage of compounds containing double bonds. For instance, butanetetracarboxylic acid can be prepared by oxidative cleavage of tetrahydrophthalic acid using nitric acid under vanadium catalysis (J. Org. Chem. 30, 1488 (1965), DE-A-30 16 225, JP 59128350 A2). This process is disadvantageous because of the aggressive reaction conditions causing some of the starting materials used and of the intermediate and end products to be decomposed by further oxidation reactions. In addition, toxic nitrogen oxides escape in the course of the reaction and can only be removed by an inconvenient gas scrub. The process by-produces nitrogenous compounds which, in the use as textile crosslinkers, lead to noticeable yellowing of the finished fabric and are removable only by inconvenient recrystallizing.

Therefore, hydrogen peroxide is a more suitable oxidizing agent, since its use gives rise to just water as reaction product. U.S. Pat. No. 3,646,130 describes the oxidative cleavage of cyclododecene with hydrogen peroxide using $Re_2O_7$ as catalyst. EP-A-0 122 804 discloses the oxidative cleavage of various olefins with hydrogen peroxide using a catalyst prepared from $H_2WO_4$, $H_3PO_4$ and a phase transfer catalyst. In EP-A-0 123 495 various intermediates obtainable by dihydroxylation of olefins are cleaved to the corresponding carboxylic acids using hydrogen peroxide and a catalytic system composed of $H_2WO_4$ and $H_3PO_4$.

EP-A-0 513 600 describes preparing carboxylic acids by oxidative work-up of olefins reacted with ozone. This reference too mentions preparing butanetetracarboxylic acid from tetrahydrophthalic anhydride. But the disadvantage with this process is the use of toxic ozone, which, moreover, is energy-intensive to prepare.

U.S. Pat. No. 5,047,582 describes the preparation of polycarboxylic acids in a two-step process. The first step is the conversion, in a non-catalyzed process, of an olefin into the corresponding dihydroxy compound which, in a second step, is cleaved by the use of various transition metal catalysts into the corresponding polycarboxylic acid.

EP-A-0 201 719 discloses preparing polycarboxylic acids such as butanetetracarboxylic acid by oxidative cleavage of olefins such as tetrahydrophthalic anhydride with hydrogen peroxide using a catalyst selected from tungstic acid, molybdic acid and heteropolyacids thereof.

EP-A-0 688 897 describes the oxidative cleavage of tetrahydrophthalic anhydride with hydrogen peroxide to form butanetetracarboxylic acid and also the use of the thusly obtained butanetetracarboxylic acid for treating cellulosic fibres.

JP 08295649 A2 describes preparing butanetetracarboxylic acid by using tungsten compounds combined with nitrogenous heterocyclic carboxylic acids as oxidation catalysts.

One disadvantage with the above-described background art is that the butanetetracarboxylic acid obtained does not possess adequate acid stability in the aqueous reaction solutions produced. The consequence is that some of the butanetetracarboxylic acid separates as a solid, the rest remaining dissolved in the aqueous phase. But such solids-containing solutions are unsuitable for treating fibres or textile materials. The butanetetracarboxylic acid therefore has to be first completely isolated by evaporating the water. This, however, is energy-intensive and hence not economical. In addition, crosslinkers in the form of solids are not very attractive; the most commonly used crosslinkers for cellulose are offered as aqueous solutions because of their better handlability. These disadvantages are the reason why polycarboxylic acids such as butanetetracarboxylic acid have hitherto not found commercial application for finishing cellulosic fibres or textile materials produced therefrom.

It is accordingly an object of the present invention to provide a process for preparing polycarboxylic acids that possess sufficient acid stability in aqueous solution and are suitable for crosslinking cellulosic fibres.

This object is achieved by a process for preparing polycarboxylic acids by 1) reacting compounds of the formulae (I) or (II)

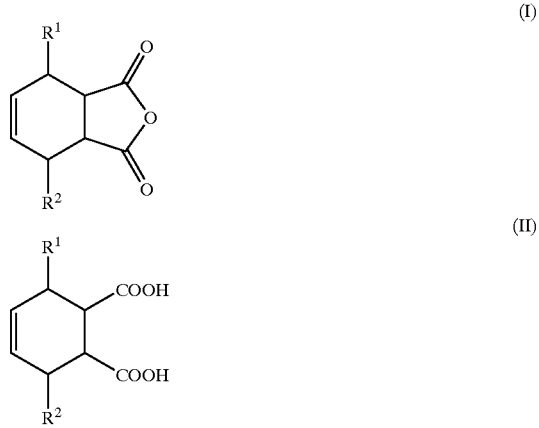

where
$R^1$ and $R^2$ are identical or different and each is H or straight-chain or branched $C_1$–$C_5$-alkyl, with compounds of the formula (III)

$$R^3XH \qquad (III)$$

where
x is O, NH or S and
$R^3$ is straight-chain or branched $C_1$–$C_{30}$-alkyl, straight-chain or branched $C_2$–$C_{30}$-alkenyl, $C_5$–$C_{12}$-cycloalkyl, —$CHR^4COOH$
where
$R^4$ is H, straight-chain or branched $C_1$–$C_5$-alkyl, —$CH_2OH$, —$CH(OH)COOH$ or —$CH_2COOH$,
or
—$(CH_2CR^5R^6Y)_nR^7$,
where
Y is O or $NR^8$,
$R^5$, $R^6$, $R^7$ and $R^8$ are independently H, straight-chain or branched $C_1$–$C_4$-alkyl, —$CH_2OH$ or —$CH_2CH_2OH$
and
n is an integer from 1 to 20
and 2) subsequent oxidation in the presence of hydrogen peroxide or of a hydrogen peroxide releaser and of a catalyst.

The invention further provides the polycarboxylic acids obtainable by this process.

The reactants used in the process of the invention are compounds of the formulae (I) or (II). They are tetrahydrophthalic acid, tetrahydrophthalic anhydride or appropriately substituted derivatives thereof. $R^1$ and $R^2$ are identical or different and are each preferably hydrogen or methyl in the formulae (I) and (II). Particular preference is given to using 1,2,3,6-tetrahydrophthalic anhydride for the reaction with compound (III).

The compounds of the formula (III) used in the process of the invention can be monofunctional, bifunctional, trifunctional or more highly functional, depending on which of the indicated meanings are assigned to $R^3$.

Preference is given to using at least bifunctional compounds of the formula (III) where
X is O and
$R^3$ is —$CHR^4COOH$,
where
$R^4$ is H, straight-chain or branched $C_1$–$C_5$-alkyl, —$CH_2OH$, —$CH(OH)COOH$ or —$CH_2COOH$, or —$(CH_2CR^5R^6Y)_nR^7$,
where
Y is O or $NR^8$ and
$R^5$, $R^6$, $R^7$ and $R^8$ are independently H, straight-chain or branched $C_1$–$C_4$-alkyl, —$CH_2OH$ or —$CH_2CH_2OH$
and
n is an integer from 1 to 10, preferably from 1 to 5.

Particular preference for use as bi- or trifunctional compounds of the formula (III) is given to the use of ethylene glycol, diethylene glycol, triethylene glycol, lactic acid, glycerol, trimethylolpropane or 2,2-bis(hydroxymethyl) propionic acid.

In a preferred embodiment, 1,2,3,6-tetrahydrophthalic anhydride is reacted with an $R^3OH$ compound where R is —$(CH_2CR^5R^6Y)_nR^7$, Y is O or $NR^8$ and $R^5$, $R^6$, $R^7$ and $R^8$ are independently H, straight-chain or branched $C_1$–$C_4$-alkyl, —$CH_2OH$ or —$CH_2CH_2OH$ and n is an integer from 1–20, preferably 1–10, especially 1 to 5.

In a particularly preferred embodiment, 1,2,3,6-tetrahydrophthalic anhydride is reacted with an $R^3OH$ compound where $R^3$ is $(CH_2CH_2O)_nH$ and n is an integer of 1 to 5, preferably 1, 2 or 3.

The reaction of compounds (I) or (II) with compound (III) in step 1) of the process according to the invention is carried out at a temperature of 50 to 250° C., preferably 90 to 150° C., and a pressure of 0 to 10 bar, preferably 0.5 to 2 bar. The reaction time is customarily 0.5–24 hours, preferably 1 to 3 hours. The reaction is preferably carried out in stirred vessels and reactors. The compounds (I) or (II) and (III) can be added in any order, preferably not in solution but as solids or liquids. The reaction can be carried out in the presence but also in the absence of a catalyst. If a catalyst is used, customary esterification catalysts, such as acids or bases, or metallic catalysts, such as titanium or tin compounds, are useful.

The as-reacted mixture of step 1) is subsequently and directly subjected, in step 2), to an oxidative cleavage using hydrogen peroxide, or a compound that releases hydrogen peroxide in situ, as oxidizing agent. Prior to the oxidative cleavage a work-up of the reaction mixture is advantageously not necessary, but can be carried out.

The oxidation in step 2) of the process according to the invention constitutes an oxidative cleavage of the double bonds in the reaction products of step 1) to form two carboxylic acid groups at two adjacent carbon atoms which are then linked by a single bond. This oxidation is carried out in the presence of a catalyst. The catalyst used is preferably a tungsten or molybdenum catalyst. Examples of suitable tungsten catalysts are tungsten oxide ($WO_3$), tungstic acid ($H_2WO_4$ or $WO_3.H_2O$), the isopolyacids and heteropolyacids of tungsten, alkali metal, alkaline earth metal and ammonium tungstates, preferably sodium tungstate ($Na_2WO_4.2H_2O$), ammonium paratungstate (($NH_4$)$_{10}$ $W_{12}O_{41}.11H_2O$) or ammonium metatungstate (($NH_4$)$_6$ $H_2W_{12}O_{40}$). Examples of suitable molybdenum catalysts are molybdenum(VI) oxide, the isopolyacids and heteropolyacids of molybdenum and also alkali metal, alkaline earth metal or ammonium molybdates.

The oxidizing agent used is hydrogen peroxide or a compound that donates hydrogen peroxide in situ. As compounds donating hydrogen peroxide in situ there can be used hydrogen peroxide addition compounds such as peroxide-urea adducts or per compounds such as perborates, percarbonates or persulphates in the form of their alkali metal salts, individually or in mixtures. Preference is given to using a hydrogen peroxide solution 30 to 60% by weight in strength. Particular preference is given to using a commercially available 50% by weight hydrogen peroxide solution.

The oxidative cleavage is carried out at a temperature of 50 to 150° C., preferably 70 to 95° C., and a pressure of 0 to 4 bar, preferably 0.5 to 2 bar. The reaction time is customarily 0.5 to 24 hours, preferably 3 to 10 hours. The reaction is customarily carried out in a stirred vessel or reactor. The hydrogen peroxide or the hydrogen peroxide releaser is customarily simply added to the reaction mixture from the first step of the process according to the invention.

The present invention provides the polycarboxylic acids obtainable by the aforementioned process. They are obtained as described in aqueous solution after the oxidative cleavage and can advantageously be used without further work-up for durable press finishing of cellulosic fibres or textile materials produced therefrom. However, it is also possible to isolate the polycarboxylic acids by evaporating the water or by precipitation.

The advantage of the polycarboxylic acids thus obtained is that they are readily water-soluble and acid-stable, ie. they are stable to precipitations even at low temperatures, unlike butanetetracarboxylic acid. The pH of the polycarboxylic acid solution obtained after step 2) of the process according to the invention is in the range from 0 to 2, but preferably the pH is not more than 1. Depending on the intended purpose, the pH of these polycarboxylic acid solutions can be adjusted with alkaline compounds to a pH of up to 10, preferably to a pH in the range from 3 to 5.

Depending on whether the compound of the formula $R^3XH$ used in the process of the invention is mono-, bi-, tri- or more highly functional and depending on the molar ratio in which the compounds of the formula (I) or (II) are used relative to the compounds of the formula (III), polycarboxylic acid mixtures can be formed in the reaction.

The use of a monofunctional $R^3XH$ compound produces via the intermediate of the formula (IV)

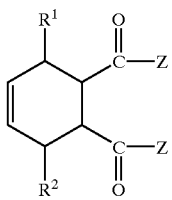
(IV)

where either one Z is OH and one Z is $XR^3$ or both are $XR^3$, the di- or tricarboxylic acids of the formula (V)

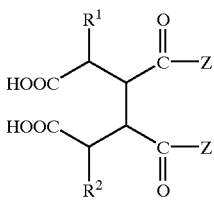
(V)

The use of a bifunctional $R^3XH$ compound where X is O, NH or S gives rise to a substantially larger number of possible polycarboxylic acids. When $R^3$ is, for example, $(CH_2CR^5R^6Y)_nH$, where Y is O or $NR^8$ and $R^5$, $R^6$ and $R^8$ are independently H or straight-chain or branched $C_1$–$C_4$-alkyl and n is an integer from 1 to 20, preferably 1 to 10, particularly preferably 1 to 5, and the compound of the formula (I) or (II) is used in a molar ratio of 2:1 relative to the compound (III), the intermediate product has the formula (VI)

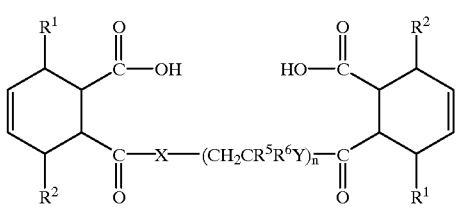
(VI)

where

X is O, NH, or S,

Y is O or $NR^8$, $R^5$, $R^6$ and $R^8$ are independently H or straight-chain or branched $C_1$–$C_4$ alkyl and n is an integer form 1 to 20, preferably 1 to 10, particularly preferably 1 to 5, and gives rise as the main product to the hexacarboxylic acid of the formula (VII)

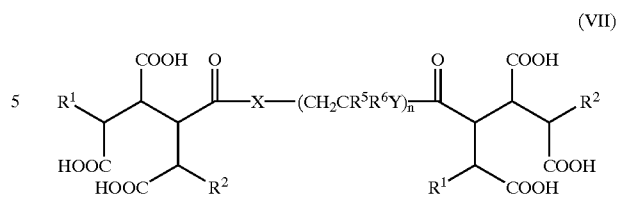
(VII)

where

X, $R^5$, $R^6$ and Y have the meanings already above mentioned for this variant.

The invention further provides for the use of the polycarboxylic acids obtainable by the process of the invention for finishing cellulosic fibres or textile or paper materials produced therefrom. Here, the polycarboxylic acids of the invention are preferably used directly in the form of the aqueous solutions that are obtained according to the process of the invention.

The invention further provides a process for finishing cellulosic fibres or textile or paper materials produced therefrom, characterized in that the cellulosic fibres or textile or paper materials produced therefrom are treated with an aqueous liquor containing the polycarboxylic acids according to the invention with or without catalysts and textile auxiliaries, preferably softeners, hand modifiers, hydrophobicizers, oleophobicizers, flame retardants or pH regulators.

By reacting with the hydroxyl groups of the cellulose, the polycarboxylic acids of the invention crosslink the amorphous parts of the fibres to some extent. This no-wrinkle and no-iron finish ensures that the textile retains its shape on wearing and washing.

Catalysts useful in the finishing of cellulosic fibres or textile or paper materials produced therefrom include for example alkali metal hypophosphites and alkali metal phosphites, preferably sodium hypophosphite or sodium phosphite. Such alkali metal hypophosphites and alkali metal phosphites are described in U.S. Pat. No. 4,820,307. Useful catalysts further include cyanamide or a compound of the formula (VIII)

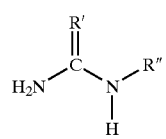
(VIII)

where

R' is NH, O or S and

R" is CN or H.

Cyanamide and the compounds of the formula (VIII) are described in U.S. Pat. No. 5,205,836.

The liquor treatment of cellulosic fibres or of textile or paper materials produced therefrom can be effected according to methods familiar to one skilled in the art, such as pad-mangling, spraying, kiss rolling or foaming. The liquor used customarily contains 10 to 100 g of active ingredient per liter, preferably 30 to 70 g of active ingredient per liter.

After application has taken place, the cellulosic fibres or textile or paper materials produced therefrom are dried at temperatures of 100 to 130° C. This drying is preferably carried on to reach a residual moisture content of 1 to 10% by weight, preferably 2 to 6% by weight, especially 3 to 4% by weight. This is followed by a heat treatment at temperatures of 130 to 220° C., preferably 140 to 180° C. The steps of drying and heat treatment can also be carried out in a single stage.

The process of the invention is useful for treating any cellulosic fibres or textile or paper materials produced therefrom. Useful cellulosic fibres include for example textile fibres of natural or regenerated cellulose or of cellulose acetate. The process can also be used for finishing blends of cellulosic and synthetic fibres. Examples of substrates which are treated are cotton, linen, rayons or paper.

The invention thus also provides cellulosic fibres or textile or paper materials treated with the polycarboxylic acids according to the invention.

EXAMPLES

I Preparation of Polycarboxylic Acids

Comparative Example I after Example 1 of EP-A-0 201 719

In a stirred vessel, 30.4 g (0.20 mol) of tetrahydrophthalic anhydride and 60 g of water are heated to 100° C. and stirred at 100° C. for half an hour. The solution is cooled down to 70° C., 1.0 g (4.0 mmol) of tungstic acid is added, 15 g (0.265 mol) of 60% hydrogen peroxide are added dropwise, and the batch is maintained at 70° C. for 2 h. 42 g (0.741 mol) of 60% hydrogen peroxide are then added, and the batch is heated to 90° C. and maintained at 90° C. for 10 h. After the reaction solution has been cooled down to room temperature, some of the carboxylic acid formed precipitates, while the rest remains dissolved in the water.

Example A1

In a stirred vessel, 228.2 g (1.5 mol) of tetrahydrophthalic anhydride and 46.6 g (0.75 mol) of ethylene glycol are heated to 100° C. with stirring. The evolving heat of reaction raises the temperature of the reaction mixture to 130° C. After cooling to 90° C., 450 g of water are added, followed by 7.5 g (30 mmol) of tungstic acid. A total of 510.3 g (7.5 mol) of 50% hydrogen peroxide are metered in over a period of 6 h. The batch is subsequently stirred at that temperature for 10 h. Cooling leaves a clear yellowy polycarboxylic acid solution. Prior to use for finishing, cellulosic fibres, 53.0 g (0.66 mol) of 50% aqueous sodium hydroxide solution are added.

Example A2

In a stirred vessel, 228.2 g (1.5 mol) of tetrahydrophthalic anhydride and 69.8 g, (1.125 mol) of ethylene glycol are heated to 100° C. with stirring. The evolving heat of reaction raises the temperature of the reaction mixture to 130° C. After cooling to 90° C., 450 g of water are added, followed by 7.5 g (30 mmol) of tungstic acid. A total of 510.3 g (7.5 mol) of 50% hydrogen peroxide are metered in over a period of 6 h. The batch is subsequently stirred at that temperature for 10 h. Cooling leaves a clear yellowy polycarboxylic acid solution. Prior to use for finishing cellulosic fibres, 49.5 g (0.62 mol) of 50% aqueous sodium hydroxide solution are added.

Example A3

In a stirred vessel, 228.2 g (1.5 mol) of tetrahydrophthalic anhydride and 46.0 g (0.5 mol) of glycerol are heated to 100° C. with stirring. The evolving heat of reaction raises the temperature of the reaction mixture to 120° C. After cooling to 90° C., 450 g of water are added, followed by 7.5 g (30 mmol) of tungstic acid. A total of 510.3 g (7.5 mol) of 50% hydrogen peroxide are metered in over a period of 6 h. The batch is subsequently stirred at that temperature for 10 h. Cooling leaves a clear yellowy polycarboxylic acid solution. Prior to use for finishing cellulosic fibres, 54.4 g (0.68 mol) of 50% aqueous sodium hydroxide solution are added.

Example A4

In a stirred vessel, 228.2 g (1.5 mol) of tetrahydrophthalic anhydride and 67.1 g (0.5 mol) of trimethylolpropane are heated to 100° C. with stirring. The evolving heat of reaction raises the temperature of the reaction mixture to 120° C. After cooling to 90° C., 450 g of water are added, followed by 7.5 g (30 mmol) of tungstic acid. A total of 510.3 g (7.5 mol) of 50% hydrogen peroxide are metered in over a period of 6 h. The batch is subsequently stirred at that temperature for 10 h. Cooling leaves a clear yellowy polycarboxylic acid solution. Prior to use for finishing cellulosic fibres, 46.0 g (0.57 mol) of 50% aqueous sodium hydroxide solution are added.

Example A5

In a stirred vessel, 228.2 g (1.5 mol) of tetrahydrophthalic anhydride and 46.6 g (0.75 mol) of ethylene glycol are heated to 100° C. with stirring. The evolving heat of reaction raises the temperature of the reaction mixture to 130° C. After cooling to 90° C., 225 g of water are added, followed by 7.5 g (30 mmol) of tungstic acid. A total of 510.3 g (7.5 mol) of 50% hydrogen peroxide are metered in over a period of 6 h. The batch is subsequently stirred at that temperature for 10 h. Cooling leaves a clear yellowy polycarboxylic acid solution. Prior to use for finishing cellulosic fibres, 53.6 g (0.67 mol) of 50% aqueous sodium hydroxide solution are added.

Example A6

In a stirred vessel, 228.2 g (1.5 mol) of tetrahydrophthalic anhydride and 135.1 g (1.5 mol) of lactic acid are heated to 100° C. with stirring. The evolving heat of reaction raises the temperature of the reaction mixture to 120° C. After cooling to 90° C., 450 g of water are added, followed by 7.5 g (30 mmol) of tungstic acid. A total of 510.3 g (7.5 mol) of 50% hydrogen peroxide are metered in over a period of 6 h. The batch is subsequently stirred at that temperature for 10 h. Cooling leaves a clear yellowy polycarboxylic acid solution. Prior to use for finishing cellulosic fibres, 57.9 g (0.72 mol) of 50% aqueous sodium hydroxide solution are added.

Example A7

In a stirred vessel, 228.2 g (1.5 mol) of tetrahydrophthalic anhydride and 100.6 g (0.75 mol) of 2,2-bis(hydroxymethyl) propionic acid are heated to 135° C. with stirring. The evolving heat of reaction raises the temperature of the reaction mixture to 145° C. After cooling to 90° C., 450 g of water are added, followed by 7.5 g (30 mmol) of tungstic acid. A total of 510.3 g (7.5 mol) of 50% hydrogen peroxide are metered in over a period of 6 h. The batch is subsequently stirred at that temperature for 10 h. Cooling leaves a clear yellowy polycarboxylic acid solution. Prior to use for finishing cellulosic fibres, 56.3 g (0.70 mol) of 50% aqueous sodium hydroxide solution are added.

Example A8

In a stirred vessel, 228.2 g (1.5 mol) of tetrahydrophthalic anhydride and 46.6 g (0.75 mol) of ethylene glycol are heated to 100° C. with stirring. The evolving heat of reaction raises the temperature of the reaction mixture to 130° C. After cooling to 90° C., 450 g of water are added, followed by 9.9 g (30 mmol) of sodium tungstate dihydrate. A total of 510.3 g (7.5 mol) of 50% hydrogen peroxide are metered in over a period of 6 h. The batch is subsequently stirred at that temperature for 10 h. Cooling leaves a clear yellowy polycarboxylic acid solution. Prior to use for finishing cellulosic fibres, 53.0 g of 50% aqueous sodium hydroxide solution are added.

II Finishing of Cotton

To finish 100% cotton having a basis weight of 110 g/m², different liquors are prepared with the composition reported in the table which follows. All ingredients of the liquor are reported in g/l.

For comparison, a liquor (C1) is prepared with the conventional formaldehydic crosslinking agent dimethyloldihydroxyethyleneurea (DMDHEU).

The cotton is first immersed in the liquors and then squeezed off on a mangle to a wet pick-up of 70 to 85%. The textile thus treated is put on a stenter and dried at 120° C. for 10 minutes and cured at 150° C. for 5 minutes.

It is then rated for DIN 53 890 crease recovery angle, DIN 53 892 dimensional change and DIN 53 895 post-wash self-smoothing performance. To determine the dimensional change and the self-smoothing performance, the samples are washed according to DIN 53 920 Method 3 A. For comparison, the corresponding values are also determined for the untreated cotton.

TABLE 1

| | Example | | | | | | | | | |
|---|---|---|---|---|---|---|---|---|---|---|
| | 1 | 2 | 3 | 4 | 5 | 6 | 7 | 8 | C1 | untreated |
| Product used | A1 | A2 | A3 | A4 | A5 | A6 | A7 | A8 | | |
| in g/l of liquor | 220 | 220 | 220 | 220 | 180 | 220 | 220 | 220 | | |
| $NaH_2PO_2$ | 30 | 30 | 30 | 30 | 30 | 30 | 30 | 30 | | |
| DMDHEU (ca.55%) | | | | | | | | | 110 | |
| $MgCl_2$ | | | | | | | | | 24 | |
| Acetic acid 60% | | | | | | | | | 1 | |
| pH | 3 | 3 | 3 | 3 | 3 | 3 | 3 | 3 | 4 | |
| Crease recovery angle W + F to DIN 53890 | 186° | 177° | 192° | 183° | 211° | 209° | 213° | 188° | 198° | 98° |
| Dimensional change W + F to DIN 53892 in % | −0.7 | −0.7 | −0.6 | −0.7 | −0.8 | −0.8 | −0.6 | −0.7 | −0.8 | −2.4 |
| Self-smoothing rating to DIN 53895 | 6 | 6 | 6 | 6 | 6 | 6 | 6 | 6 | 6 | 1 |

What is claimed is:

1. A process for preparing polycarboxylic acids comprising
   1) reacting a compound of the formulas (I) or (II)

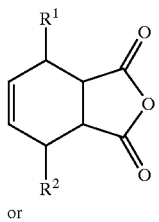

(I)

or

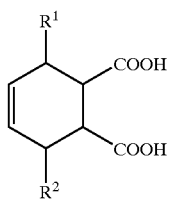

(II)

wherein $R^1$ and $R^2$ are identical or different and each is H or straight-chain or branched $C_1$–$C_5$-alkyl, with a compound of the formula (III)

$$R^3XH$$

wherein
X is O, NH, or S and
$R^3$ is straight-chain or branched $C_1$–$C_{30}$-alkyl; straight-chain or branched $C_2$–$C_{30}$-alkenyl; $C_5$–$C_{12}$-cycloalkyl; —$CHR^4COOH$ wherein $R^4$ is H, straight-chain or branched $C_1$–$C_5$-alkyl, —$CH_2OH$, —CH(OH)COOH, or —$CH_2COOH$; or —$(CH_2CR^5R^6Y)_nR^7$ wherein Y is O or $NR^8$, $R^5$, $R^7$, and $R^8$ are independently H, straight-chain or branched $C_1$–$C_4$-alkyl, —$CH_2OH$, or —$CH_2CH_2OH$, and n is an integer from 1 to 20, and 2) oxidizing the product from step 1) in the presence of hydrogen peroxide or a hydrogen peroxide releaser and of a catalyst.

2. A process according to claim 1 wherein in formulas (I) and (II) $R^1$ and $R^2$ are independently hydrogen or methyl.

3. A process according to claim 1 wherein in formula (III) X is O and
$R^3$ is —$CHR^4COOH$ wherein $R^4$ is H, straight-chain or branched $C_1$–$C_5$-alkyl, —$CH_2OH$, —CH(OH)COOH, or —$CH_2COOH$; or —$(CH_2CR^5R^6Y)_nR^7$ wherein Y is O or $NR^8$, $R^5$, $R^6$, $R^7$, and $R^8$ are independently H, straight-chain or branched $C_1$–$C_4$-alkyl, —$CH_2OH$, or —$CH_2CH_2OH$, and n is an integer from 1 to 10.

4. A process according to claim 1 wherein the compound of formula (III) is ethylene glycol, diethylene glycol, triethylene glycol, lactic acid, glycerol, trimethylolpropane, or 2,2-bis(hydroxymethyl)propionic acid.

5. A process according to claim 1 wherein reaction step 1) comprises reacting 1,2,3,6-tetrahydrophthalic anhydride with a compound of the formula $R^3OH$ wherein $R^3$ is —$(CH_2CR^5R^6Y)_nR^7$, Y is O or $NR^8$, $R^5$, $R^6$, $R^7$, and $R^8$ are independently H, straight-chain or branched $C_1$–$C_4$-alkyl, —$CH_2OH$, or —$CH_2CH_2OH$, and n is an integer from 1 to 20.

6. A process according to claim 1 wherein oxidation step 2) is carried out in the presence of a tungsten or molybdenum catalyst.

7. A process according to claim 6 wherein the catalyst is tungsten oxide, tungstic acid, an isopolyacid or heteropolyacid of tungsten, an alkali metal, alkaline earth metal or ammonium tungstate, molybdenum(VI) oxide, an isopolyacid or heteropolyacid of molybdenum, or an alkali metal, alkaline earth metal or ammonium molybdate.

8. A process according to claim 1 wherein reaction step 1) is carried out at a temperature of 50 to 250° C. and a pressure of 0 to 10 bar and oxidation step 2) is carried out at a temperature of 50 to 150° C. and a pressure of 0 to 4 bar.

9. A polycarboxylic acid having the formula

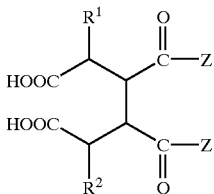

wherein

R$^1$ and R$^2$ are identical or different and each is H or straight-chain or branched C$_1$–C$_5$-alkyl, either one Z is OH and the other Z is XR$^3$ or both Z are XR$^3$, X is O, NH, or S, and R$^3$ is straight-chain or branched C$_2$–C$_{30}$-alkenyl; C$_5$–C$_{12}$-cycloalkyl; —CHR$^4$COOH wherein R$^4$ is H, straight-chain or branched C$_1$–C$_5$-alkyl or —CH$_2$COOH; —(CH$_2$CR$^5$R$^6$Y)$_n$R$^7$ wherein Y is O or NR$^8$, R$^5$, R$^6$, R$^7$, and R$^8$ are independently H or straight-chain or branched C$_1$–C$_4$-alkyl, and n is an integer from 1 to 20.

10. A method comprising finishing a cellulosic fiber or a textile or paper material produced from a cellulosic fiber with a polycarboxylic acid according to claim 9.

11. A method comprising finishing a cellulosic fiber or a textile or paper material produced from a cellulosic fiber with a polycarboxylic acid according to claim 9 in the presence of a catalyst and/or a textile auxiliary.

12. A method according to claim 11 wherein the catalyst is an alkali metal hypophosphite, an alkali metal phosphite, cyanamide, or a compound of the formula

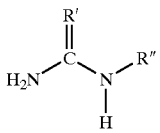

wherein R' is NH, O, or S, and R" is CN or H.

13. A cellulosic fiber or a textile or paper material produced from a cellulosic fiber that is treated with polycarboxylic acid according to claim 9.

14. A polycarboxylic acid obtained by a process consisting essentially of:

(1) reacting a compound of the formula (I) or (II)

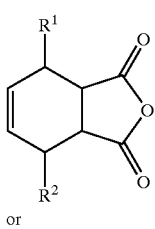

or

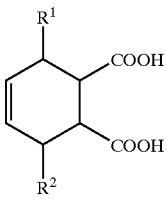

with a compound of the formula (III)

R$^3$XH  (III)

and (2) oxidizing the product from step 1 in the presence of hydrogen peroxide or a hydrogen peroxide releaser catalyst, wherein R$^1$ and R$^2$ are identical or different and each is H or straight-chain or branched C$_1$–C$_5$-alkyl, X is O, OH, or S and R$^3$ in the compound of the formula (III) is (I) —CHR$^4$COOH wherein R$^4$ is —CH$_2$OH or —CH(OH)COOH, or (II) —CH$_2$CR$^5$R$^6$Y)$_m$R$^7$ wherein Y is O or NR$^8$, wherein R$^5$, R$^6$, R$^7$, and R$^8$ are independently H, straight-chain or branched C$_1$–C$_4$-alkyl, —CH$_2$OH, or —CH$_2$CH$_2$OH, and n is an integer from 1 to 20, with the provisos that (1) R$^8$ is hydrogen and/or at least one of R$^5$, R$^6$, or R$^7$ is —CH$_2$OH or —CH$_2$CH$_2$OH, and (2) the polycarboxylic acid is not a polycarboxylic acid having the formula

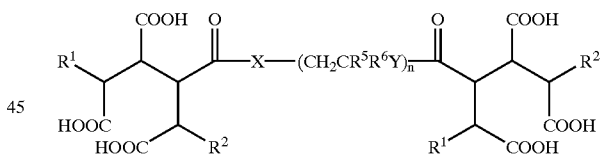

wherein

R$^1$ and R$^2$ are identical or different and each is H or straight-chain or branched C$_1$–C$_5$-alkyl, X is O, NH, or S, and Y is O or NR$^8$, R$^5$, R$^6$ and R$^8$ are independently H or straight-chain or branched C$_1$–C$_4$ alkyl, and n is an integer from 1 to 20.

15. A method comprising finishing a cellulosic fiber or a textile or paper material produced from a cellulosic fiber with a polycarboxylic acid according to claim 14.

16. A method comprising finishing a cellulosic fiber or a textile or paper material produced from a cellulosic fiber with a polycarboxylic acid according to claim 14 in the presence of a catalyst and/or a textile auxiliary.

17. A method according to claim 16 wherein the catalyst is an alkali metal hypophosphite, an alkali metal phosphite, cyanamide, or a compound of the formula

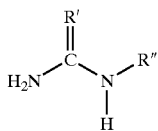

wherein R' is NH, O, or S, and R'' is CN or H.

18. A cellulosic fiber or a textile or paper material produced from a cellulosic fiber that is treated with a polycarboxylic acid according to claim 14.

19. A polycarboxylic acid having the formula

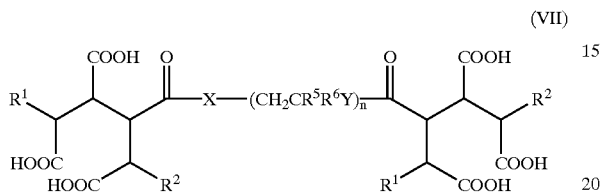

(VII)

wherein
$R^1$ and $R^2$ are identical or different and each is H or straight-chain or branched $C_1$–$C_5$-alkyl,
X is O, NH, or S,
Y is O or $NR^8$,
$R^5$, $R^6$ and $R^8$ are independently H or straight-chain or branched $C_1$–$C_4$ alkyl, and
n is an integer from 1 to 20.

20. A method comprising finishing a cellulosic fiber or a textile or paper material produced from a cellulosic fiber with a polycarboxylic acid according to claim 19.

21. A method comprising finishing a cellulosic fiber or a textile or paper material produced from a cellulosic fiber with a polycarboxylic acid according to claim 19 in the presence of a catalyst and/or a textile auxiliary.

22. A method according to claim 21 wherein the catalyst is an alkali metal hypophosphite, an alkali metal phosphite, cyanamide, or a compound of the formula

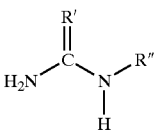

wherein R' is NH, O, or S, and R'' is CN or H.

23. A cellulosic fiber or a textile or paper material produced from a cellulosic fiber that is treated with a polycarboxylic acid according to claim 19.

* * * * *